US009738842B2

(12) United States Patent
Scott

(10) Patent No.: US 9,738,842 B2
(45) Date of Patent: Aug. 22, 2017

(54) PROCESS AND APPARATUS FOR PURIFYING A FATTY MIXTURE AND RELATED PRODUCTS INCLUDING FUELS

(71) Applicant: Argent Energy Group Limited, Motherwell (GB)

(72) Inventor: Michael Scott, Motherwell (GB)

(73) Assignee: Argent Energy (UK) Limited, North Lanarkshire (GB)

( * ) Notice: Subject to any disclaimer, the term of this patent is extended or adjusted under 35 U.S.C. 154(b) by 0 days.

(21) Appl. No.: 14/897,815

(22) PCT Filed: Jun. 19, 2014

(86) PCT No.: PCT/GB2014/051875
§ 371 (c)(1),
(2) Date: Dec. 11, 2015

(87) PCT Pub. No.: WO2014/202979
PCT Pub. Date: Dec. 24, 2014

(65) Prior Publication Data
US 2016/0137936 A1 May 19, 2016

(30) Foreign Application Priority Data

Jun. 19, 2013 (GB) .................................. 1310960.8
Jun. 19, 2013 (GB) .................................. 1310961.6
Jun. 19, 2013 (GB) .................................. 1310962.4

(51) Int. Cl.
*C10L 1/02* (2006.01)
*C11B 3/16* (2006.01)
(Continued)

(52) U.S. Cl.
CPC .............. *C10L 1/026* (2013.01); *C07C 67/03* (2013.01); *C07C 67/08* (2013.01); *C07C 67/58* (2013.01); *C10G 3/00* (2013.01); *C10G 3/40* (2013.01); *C10G 33/00* (2013.01); *C11B 3/001* (2013.01); *C11B 3/006* (2013.01); *C11B 3/008* (2013.01);
(Continued)

(58) Field of Classification Search
USPC ........................................... 44/385; 554/179
See application file for complete search history.

(56) References Cited

U.S. PATENT DOCUMENTS 3,428,660 A 2/1969 Morren
3,519,662 A 7/1970 Gruver, Jr. et al.
(Continued)

FOREIGN PATENT DOCUMENTS

CN 101760263 6/2010
CN 102492494 6/2012
(Continued)

*Primary Examiner* — Ellen McAvoy
*Assistant Examiner* — Chantel Graham
(74) *Attorney, Agent, or Firm* — Willis IP; Ryan Willis

(57) ABSTRACT

There is described a process and an apparatus for purifying a mixture and related products. In particular, there is described a process and an apparatus for purifying a mixture comprising fats, oils and greases as are typically found in sewer waste. The process involves heating, acidifying and separating the mixture. The apparatus used includes a heating and separation device for separating into a solid fraction, an organic liquid fraction and an aqueous liquid fraction. Apparatus such as a three phase separation unit and a rotary vacuum filter may also be used.

28 Claims, 2 Drawing Sheets

(51) Int. Cl.

| | | |
|---|---|---|
| *C11B 3/00* | (2006.01) | |
| *C10G 33/00* | (2006.01) | |
| *C10G 3/00* | (2006.01) | |
| *C07C 67/03* | (2006.01) | |
| *C07C 67/08* | (2006.01) | |
| *C07C 67/58* | (2006.01) | |
| *C11C 3/00* | (2006.01) | |
| *C11B 3/04* | (2006.01) | |
| *C11B 3/12* | (2006.01) | |
| *C11C 3/10* | (2006.01) | |
| *B01D 21/26* | (2006.01) | |
| *B03D 1/14* | (2006.01) | |

(52) U.S. Cl.
CPC ........... *C11B 3/04* (2013.01); *C11B 3/12* (2013.01); *C11B 3/16* (2013.01); *C11C 3/003* (2013.01); *C11C 3/10* (2013.01); *B01D 21/262* (2013.01); *B03D 1/1431* (2013.01); *C10G 2300/1003* (2013.01); *C10G 2300/201* (2013.01); *C10G 2400/04* (2013.01); *C10L 2200/0446* (2013.01); *C10L 2200/0476* (2013.01); *C10L 2270/026* (2013.01); *C10L 2270/04* (2013.01); *C10L 2290/06* (2013.01); *C10L 2290/18* (2013.01); *C10L 2290/542* (2013.01); *C10L 2290/543* (2013.01); *C10L 2290/544* (2013.01); *C10L 2290/547* (2013.01); *Y02E 50/13* (2013.01); *Y02P 30/20* (2015.11)

(56) References Cited

U.S. PATENT DOCUMENTS

| | | | |
|---|---|---|---|
| 4,364,743 A | 12/1982 | Erner | |
| 6,822,105 B1 | 11/2004 | Luxem et al. | |
| 7,622,600 B1 | 11/2009 | Marr | |
| 2005/0232956 A1 | 10/2005 | Bist | |
| 2006/0070912 A1 | 4/2006 | Khan | |
| 2007/0196250 A1 | 8/2007 | Leveson | |
| 2007/0232817 A1 | 10/2007 | Pereira et al. | |
| 2009/0030219 A1 | 1/2009 | Su | |
| 2010/0059450 A1 | 3/2010 | Lafosse et al. | |
| 2010/0059451 A1 | 3/2010 | Gallo et al. | |
| 2010/0087671 A1 | 4/2010 | Lemke | |
| 2010/0202933 A1 | 8/2010 | Iyer | |
| 2010/0305346 A1 | 12/2010 | Hara et al. | |
| 2010/0330615 A1 | 12/2010 | Neto | |
| 2011/0023353 A1 | 2/2011 | Ciciulla | |
| 2011/0166378 A1 | 7/2011 | Pelly | |
| 2011/0192076 A1 | 8/2011 | Hess et al. | |
| 2011/0197497 A1 | 8/2011 | Jiang | |
| 2012/0123140 A1 | 5/2012 | Jackam et al. | |
| 2012/0183354 A1 | 7/2012 | Redmile-Gordon et al. | |
| 2014/0020282 A1 | 1/2014 | Lavella, Sr. | |

FOREIGN PATENT DOCUMENTS

| | | |
|---|---|---|
| CN | 102585927 | 7/2012 |
| CN | 103571630 | 2/2014 |
| FR | 2894977 | 6/2007 |
| GB | 1044311 | 9/1966 |
| JP | 2004105915 | 4/2004 |
| JP | 2008081730 | 4/2008 |
| WO | 2004085579 | 10/2004 |
| WO | 2010043212 | 4/2010 |
| WO | 2012068651 | 5/2012 |
| WO | 2014202979 | 12/2014 |

PROCESS AND APPARATUS FOR PURIFYING A FATTY MIXTURE AND RELATED PRODUCTS INCLUDING FUELS

CROSS REFERENCE TO RELATED APPLICATIONS

This application claims priority under 35 U.S.C. §119 to United Kingdom patent application serial numbers 1310960.8, 1310961.6, and 1310962.4, all filed on Jun. 19, 2013, the disclosures of which are incorporated herein by reference, and is a national stage application of Patent Cooperation Treaty application serial number PCT/GB14/051875, filed Jun. 19, 2014.

FIELD OF THE INVENTION

This invention relates to a process and an apparatus for purifying a mixture and related products. In particular, the invention relates to a process and an apparatus for purifying a mixture comprising fats, oils and greases as are typically found in sewer waste.

BACKGROUND OF THE INVENTION

The following description will refer particularly to mixtures comprising fats, oils and greases as are typically found in sewer waste. However, the invention is also applicable to mixtures from which it is desirable to extract or separate an organic substance from solids and/or aqueous substances.

The term "biodiesel" is used to refer to vegetable or animal fat, oil or grease derived diesel, consisting of long-chain alkyl methyl (ethyl or propyl) esters. Biodiesel is distinct from petroleum diesel (also known as petrodiesel or petroleum derived diesel), which is a specific fractional distillate of petroleum fuel oil.

Fats, oils and greases are constituents of sewer waste or sewage, and are referred to commonly as "sewer grease". Fats are triglycerides (triesters of glycerol and any of several fatty acids), and may be either solid or liquid at room temperature. Oils are neutral, non-polar molecules with a high hydrocarbon content. Greases are semisolid lubricants which generally consist of a soap emulsified with mineral or vegetable oil. Greases can be of natural origin, and can be either vegetable or animal derived.

Fats, oils and greases gather in sewer waste and are very problematic, leading to the blockage of sewerage systems. Thus they are generally considered a problematic waste product. Nevertheless, such fats, oils and greases do contain hydrocarbons, which are a potential source of valuable products such as, for example, fuels.

Typically, however, sewer grease comprises a number of waste products and aqueous materials. For example, sewer grease contains a large amount of insoluble debris and many different chemicals. Furthermore, sewer grease is very viscous and has a relatively high melting point, which is why it causes sewerage systems to become blocked.

Fuels are required to have a certain degree of purity in order to be usable. For example, biodiesel (which can in principle be made from other hydrocarbon based materials) needs to have a certain purity or FAME (fatty acid methyl ester) value in order to be usable in engines or the like. Current legislation (EN 14214) states that in order to be suitable for use in engines, biodiesel must have a minimum ester content of 96.5%. In general, the starting material used has a large impact on the quality of the biodiesel obtained.

Therefore, due to the impure and unpredictable nature of sewer grease, it has not been practicable to use sewer grease as a source of fats, oils and greases for producing fuels such as biodiesel.

It is an object of the present invention to overcome or mitigate at least some of the problems of the prior art. A further object of the invention is to obtain a material from fats, oils and/or greases that is usable to produce further products such as, for example, fuels such as biodiesel and/or the precursors thereof.

SUMMARY OF THE INVENTION

According to a first aspect of the invention there is provided a process for purifying a mixture comprising fat, oil and/or grease, said process comprising the steps of:
  (i) initial heating of the mixture so that it is flowable;
  (ii) acidifying the mixture;
  (iii) separating the mixture into a solid fraction, an organic liquid fraction and an aqueous liquid fraction; and
  (iv) removing said solid and said aqueous liquid fractions from the mixture.

The mixture may be a multi-phase mixture and may comprise at least an organic (liquid) phase (fraction), an aqueous (liquid) phase (fraction) and a solid phase (fraction).

The separating of the mixture into a solid fraction, an organic liquid fraction and an aqueous liquid fraction may be subsequent to the acidification step.

The removal of the solid and aqueous liquid fractions from the mixture may be subsequent to the acidification step.

The process may comprise the additional step of initial separation of the mixture into an initial solid fraction, an initial organic liquid fraction and/or an initial aqueous liquid fraction, before the acidification step.

The process may comprise the additional step of initial removal of the initial solid and/or initial aqueous liquid fractions from the mixture, before the acidification step.

Initial heating of the mixture so that it is flowable may comprise heating the mixture to between approximately 55° C. and approximately 65° C., optionally between approximately 57° C. to approximately 63° C., optionally approximately 60° C.

The acidification may comprise adjusting the pH to less than or equal to approximately pH 5. The pH is usefully between approximately pH 4.7 and approximately pH 4.8.

The acidification may comprise adding acid to the mixture at a rate of between approximately 1.5 kg per hour to approximately 2.5 kg per hour. Optionally the acid is phosphoric acid.

The acidification may comprise adding water to the mixture at a rate of between approximately 80 kg per hour and approximately 100 kg per hour.

Without wishing to be bound by theory, the acidification process is believed to precipitate impurities out of solution; in particular soaps and detergents, and/or other such tensides, emulsifiers, dispersing and/or wetting agents. This is also believed to mitigate emulsification, therefore better enabling separation of aqueous and organic phases.

The process may comprise the further step of pasteurising the mixture, optionally before the mixture is acidified.

The pasteurisation may comprise heating the mixture to between approximately 90° C. and approximately 100° C., optionally between approximately 92° C. and approximately 98° C., optionally approximately 95° C.

The inventors have found that using these temperatures also enables better recovery of fats, oils and greases.

The pasteurisation may comprise heating the mixture for between approximately 4 hours and approximately 6 hours, optionally between approximately 4.5 and approximately 5.5 hours, optionally approximately 5 hours.

The process may comprise the further step of removing debris from the mixture, optionally after initial heating and before acidification.

The separation may comprise the simultaneous separation and discharge of said solid fraction, organic liquid fraction and aqueous liquid fraction.

The separation may be carried out using a three phase separation unit.

The three phase separation unit may be a horizontal decanter centrifuge.

The three phase separation unit may be a counter current decanter centrifuge.

The three phase separation unit may be operated at a bowl speed of from about 3,000 to about 4,000 RPM.

The three phase separation unit may be operated at a scroll speed of from about 10 to about 20 RPM.

The process may comprise the further step of homogenising the mixture, optionally after acidification and prior to separation.

The homogenisation may comprise heating the mixture to between approximately 85° C. and approximately 95° C.

The homogenisation may comprise injecting steam into the mixture at a pressure of between approximately 5 bar(g) (600 kPa) and approximately 7 bar(g) (800 kPa).

The homogenisation may comprise agitation, optionally by way of a mechanical mixer.

The process may comprise the further step of filtering the mixture after removing said solid and said aqueous liquid fractions therefrom.

Filtering may be carried out using a rotary vacuum filter.

The rotary vacuum filter may comprise a layer of wood flour around the circumference thereof, and through which the mixture is filtered.

The wood flour may be cellulose fibre, optionally cellulose fibre 110.

The mixture may be heated to between approximately 65° C. and approximately 85° C., optionally between approximately 75° C. and approximately 85° C., optionally between approximately 72° C. and approximately 83° C., optionally approximately 80° C.

The rotary vacuum filter may be operated at a cutting rate of from approximately 100 to approximately 200 micrometers per revolution.

The rotary vacuum filter may be operated at a rotational speed of from approximately 1 to approximately 2.5 RPM.

The process may comprise the further step of recovery of organic liquids from aqueous liquids.

The recovery may comprise a dissolved air flotation process.

The dissolved air flotation process may be carried out at a temperature of approximately 45° C. or less.

According to a second aspect of the invention there is provided a purified mixture obtainable, obtained or directly obtained by the process of the first aspect.

According to a third aspect of the invention, there is provided a fuel obtainable, obtained or directly obtained from the purified mixture of the second aspect, the fuel optionally being biodiesel.

According to a fourth aspect of the invention, there is provided a fuel blend comprising the fuel of the third aspect, the fuel blend comprising biodiesel and petroleum biodiesel.

According to a fifth aspect of the invention, there is provided the use of the purified mixture obtainable, obtained or directly obtained by the first aspect in the preparation of a fuel, the fuel optionally being biodiesel.

According to a sixth aspect of the invention, there is provided an apparatus for purifying a mixture comprising fat, oil and/or grease, said apparatus comprising:
(i) a heating device configured to heat the mixture;
(ii) an inlet for introducing acidification conditions to the mixture; and
(iii) a separation device configured to separate the mixture into a solid fraction, an organic liquid fraction and an aqueous liquid fraction.

The apparatus may further comprise a device for removing the solid fraction from the mixture.

The device for removing the solid fraction from the mixture may comprise a mesh filter, optionally an inline mesh filter, optionally a duplex inline mesh filter.

The separation device may be configured to simultaneously separate and discharge the solid fraction, organic liquid fraction and aqueous liquid fraction.

The separation device may be a three phase separation unit, optionally a horizontal decanter centrifuge, optionally a counter current decanter centrifuge.

The three phase separation unit may be configured to operate at a bowl speed of about 3,000 to about 4,000 RPM.

The three phase separation unit may be configured to operate at a scroll speed of about 10 to about 20 RPM.

The apparatus may further comprise a rotary vacuum filter.

The rotary vacuum filter may comprise a layer of wood flour around the circumference thereof, and through which the mixture is filtered.

The wood flour may be cellulose fibre, optionally cellulose fibre 110.

The rotary vacuum filter may be configured to operate at a cutting rate of from approximately 100 to approximately 200 micrometers per revolution.

The rotary vacuum filter may be configured to operate at rotational speed of from approximately 1 to approximately 2.5 RPM.

The apparatus may further comprise a recovery device configured to recover organic liquids from aqueous liquids, optionally a dissolved air flotation device.

The apparatus may further comprise a homogenisation device, configured to homogenise the mixture. The homogenisation device may be a mechanical mixer configured to agitate the mixture.

The mechanical mixer may be a rotating mechanical mixer. The mechanical mixer may be a static inline mixer.

The apparatus may further comprise a pasteurisation device, configured to pasteurise the mixture.

BRIEF DESCRIPTION OF THE DRAWINGS

Embodiments of the invention will now be described, by way of example only, with reference to the drawings, in which.

DETAILED DESCRIPTION

Figure 1:
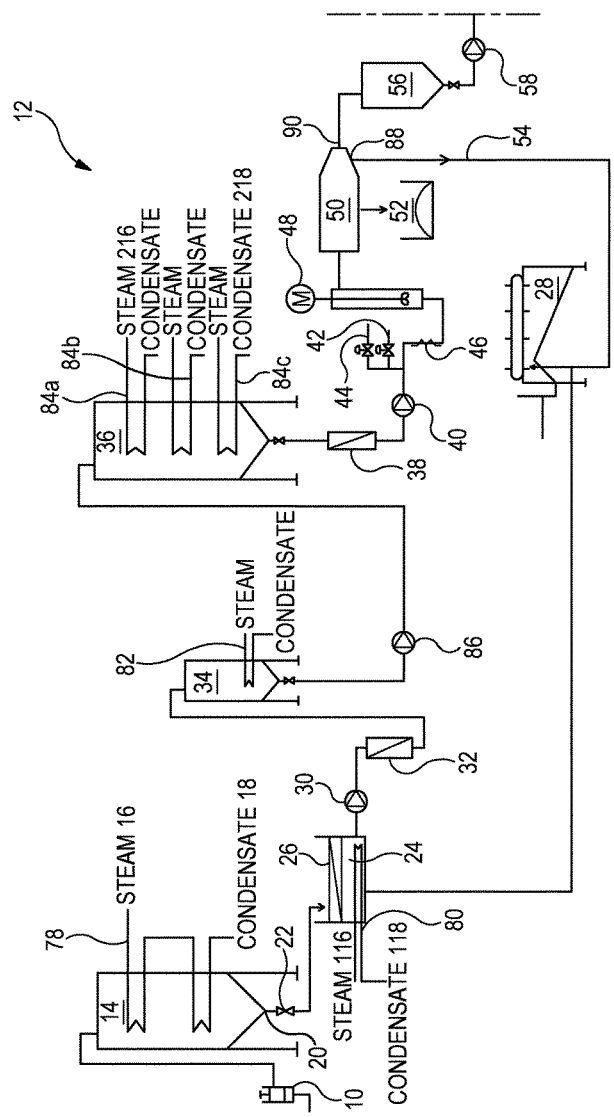
FIG. 1 is schematic diagram of a process in accordance with one embodiment of the invention.
Figure 1:
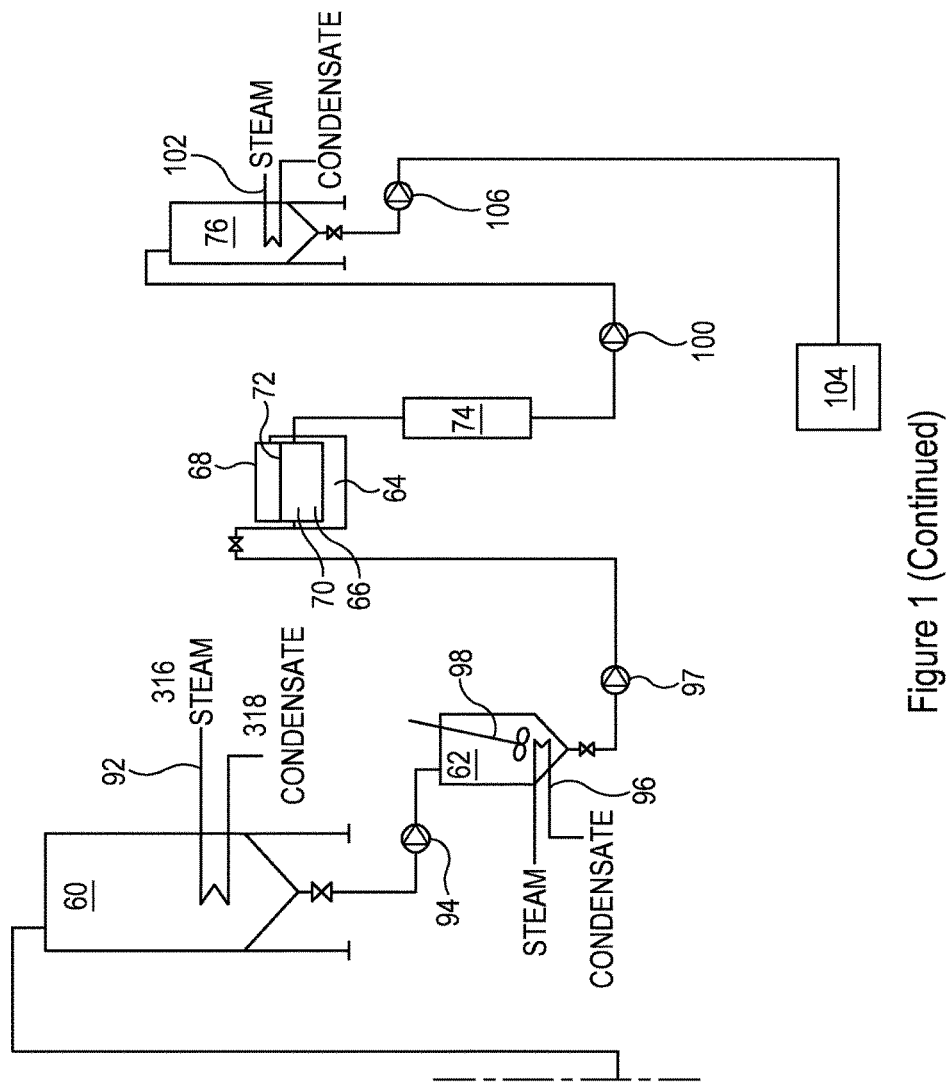

Referring to FIG. 1, the first step involves taking a fat, oil and grease mixture from a sewage treatment works (not shown) and transferring these to a tanker (not shown). The tanker then transports the mixture to a treatment plant 12.

The mixture is a multi-phase mixture, comprising at least an organic (liquid) phase, an aqueous (liquid) phase and a solid phase.

The mixture is then subjected to initial heating to 60° C. using steam injection in order to make the mixture sufficiently mobile for processing (i.e., the mixture is made flowable). A range of temperatures between 55° C. and 65° C., or typically 57° C. and 63° C., can be used.

The mixture is then transferred using a piston pump 10 (VRH 250) to a reception/dewatering tank 14, where the mixture is heated to 95° C. using a double heating coil 78 (a heating device) and/or using steam injection (steam in 16, condensate out 18) for a time of approximately 5 hours, which pasteurises the mixture. The heating time may, however, be between approximately 4 hours and approximately 6 hours, or between approximately 4.5 hours and 5.5 hours. Heating to 95° C. also improves oil, water and solid separation. A range of temperatures between 90° C. and 100° C. or, typically 92° C. and 98° C., can be used. The organic phase (also referred to as the oil phase or the lipid phase), aqueous phase and solids begin to separate out in the reception/dewatering tank 14. The reception/dewatering tank 14 has an 8" (approximately 20 cm) outlet 20 to help prevent blockage when the mixture is discharged from the reception/dewatering tank 14. The flow is controlled by an 8" (approximately 20 cm) manual knife valve 22, which will cut through debris, again helping to prevent blockage of the outlet 20.

After heating, the mixture is discharged from the reception/dewatering tank 14. As the mixture from the reception/dewatering tank 14 has begun to separate, the mixture discharged is initially primarily aqueous phase and settled solids. This enters the open topped tank 24 through an integral 6 mm perforated mesh 26 which removes large particulate matter (debris). The aqueous phase is diverted to an effluent treatment facility 28 until the mixture being discharged from the reception/dewatering tank 14 changes from aqueous phase to organic phase. The solids retained by the filter mesh 26 are removed periodically throughout the process to prevent the mesh 26 from becoming blocked. The mixture has now been through a primary screening.

The melting bath/open topped tank 24 has a steam/heating coil 80 (steam in 116, condensate out 118) located in the bottom to maintain a temperature sufficient to keep the mixture in a mobile, flowable state (i.e., to prevent solidification). Any residual organic phase in the aqueous phase is recovered through a dissolved air flotation unit 28. This recovered organic phase can be introduced back into the process at a later stage, ensuring minimum losses.

A dissolved air flotation unit is a water treatment process that clarifies water or such like by the removal of suspended matter such as solids or organic liquids, such as fats, oils and greases. The removal is achieved by first reacting the mixture in the unit with a coagulant (for example, ferric or aluminium sulphate, or ferric or aluminium chloride), and then adjusting the pH to between pH 5 and pH 7 using an alkali or base such as, for example, sodium hydroxide. The resultant colloid is then removed using a polymer based flocculant ionic polyacrylamide (Millfloc™ V39™). The flocs are then removed by dissolving air in the water under pressure and then releasing the air at atmospheric pressure in a flotation tank or basin.

The released air forms small bubbles which adhere to the suspended matter causing the suspended matter to float to the surface of the water where it may then be removed by a skimming device.

Referring again to FIG. 1, after primary screening, a centrifugal pump 30 is used to transfer the mixture via a 3 mm mesh inline filter 32 to a heated conical consolidation tank 34 with a heating coil 82, where further settling occurs. After settling, the aqueous phase and the solids are decanted into an appropriate waste receptacle (not shown) for disposal.

The organic phase from the consolidation tank 34 is then transferred to a heated and lagged holding tank 36 (heating by a heating coil 84a, 84b, 84c, steam in 216, condensate out 218), using a centrifugal pump 86, and where the mixture is held prior to further purification. The mixture from this tank 36 is drawn through a duplex inline filter 38 with a 2 mm mesh by a Waukesha™ gear pump 40 at a rate of between 1,500 and 2,500 kg per hour. During this transfer process, water and 75% by weight phosphoric acid (80 to 100 kg per hour and 1.5 to 2.5 kg per hour respectively) are injected via inlets 42 and 44 respectively into the mixture, before the mixture enters a static inline mixer 46. The acidification step alters the pH to pH 5 or less. However, the pH can usefully be between approximately pH 4.7 and approximately pH 4.8. The mixture is then heated by introducing steam at 5 to 7 bar(g) (600 to 800 kPa) into mixer 46, heating the mixture to 85° C. to 95° C. Mixing is further enhanced using a rotating mechanical mixer 48 that is situated in line, ensuring that the mixture is homogenised before being separated.

The homogenised mixture is transferred to a three phase separation unit 50, which is a counter current horizontal decanter centrifuge (Z4E-3/441 g TRICANTER®). The three phase separation unit 50 is run at a bowl speed of 3,400 RPM (revolutions per minute) and a scroll speed of 12 to 14 RPM. The separated solids drop into a suitable receptacle 52 underneath the three phase separation unit 50. The aqueous phase is removed through an outlet port 88 under vacuum and is piped to the drainage system 54. Organic materials in the aqueous phase are recovered using a dissolved air flotation unit 28. The separated organic phase passes over a weir (not shown) located within the separation unit 50 and is removed through an outlet port 90 under gravity, before being piped to a buffer tank 56. The organic phase is then transferred using a positive displacement pump 58 to a heated and lagged bulk storage tank 60 equipped with a heating element 92. The separation step involves the simultaneous separation and discharge of a solid fraction, an organic liquid fraction (phase) and an aqueous liquid fraction (phase).

The three phase separation unit 50 may be used with the following settings:

Bowl speed: 3,000 to 4,000 RPM; and/or
Scroll speed: 10 to 20 RPM.

To ensure that the organic phase is suitable for high pressure/temperature esterification (one of the first stages in preparing the material for biodiesel production) the organic phase is subjected to a final filtration step which removes any remaining solid contaminants. The organic phase is transferred using a centrifugal pump 94 from the bulk holding tank 60 (steam in 316, condensate out 318) into a heated buffer tank 62 equipped with a heating element 96 and a mixer 98 before being pumped using positive displacement pump 97 into the sump 64 of a rotary vacuum filter 66 (ROTAVAC®). The rotary vacuum filter 66 comprises a layer (or bed) of wood flour 68 around the circumference thereof, and through which the mixture is filtered. The wood flour 68 is initially mixed with organic phase material before being drawn on the drum 70 of the rotary vacuum filter 66. The organic phase is drawn from the sump 64 through the bed 68 leaving any contamination behind. A knife 72 cuts continually into the bed 68 exposing a new filter area, this ensures that an optimum filtration rate is maintained. The mixture is maintained at a temperature of 80° C. during the filtration process. However, the temperature may be between approximately 75° C. and approximately 85° C., or between approximately 72° C. and approximately 83° C., or between 65° C. and 85° C.

The rotary vacuum filter 66 may be used with the following settings:

Cutting rate: 100 to 200 micrometers per revolution;
Wood flour type/grade: cellulose fibre 110; and/or
Rotational speed: 1 to 2.5 RPM.

Once filtered, the purified mixture is drawn into the filtrate tank 74 for storage. The purified mixture is then transferred using a positive displacement pump 100 to a final tank 76, equipped with a heating coil 102 before being transferred to a high pressure esterification plant 104 by way of a pump 106. This plant 104 prepares the purified mixture for further processing, such as the biodiesel formation process.

The purified mixture obtained from the process described can be used as a starting material for a further process used to produce fuels such as biodiesel.

The whole process as outlined above is usefully carried out at a temperature of at least 60° C., apart from the dissolved air flotation process, which is carried out at a lower temperature as outlined above.

In one embodiment there is provided a purified mixture prepared by the process outlined herein.

In a further embodiment there is provided a fuel prepared from the purified mixture described herein. In one embodiment the fuel is biodiesel.

In one embodiment there is provided a fuel prepared from the purified mixture of the process described herein. In one embodiment the fuel is biodiesel.

The present invention thus provides a process for purifying fats, oils and greases (from sewer grease, for example) such that they may be used to prepare fuels such as biodiesel. Thus, a valuable precursor to biodiesel can be obtained from an otherwise waste material. Previously, it had been considered impracticable to purify such materials and/or to obtain biodiesel or the precursors thereof from such highly contaminated starting materials. However, the inventors have surprisingly shown that such contaminated starting materials can be processed to provide a biodiesel precursor and biodiesel.

While this invention has been described with reference to the sample embodiments thereof, it will be appreciated by those of ordinary skill in the art that modifications can be made to the structure and elements of the invention without departing from the spirit and scope of the invention as a whole.

The invention claimed is:

1. A process for purifying a mixture comprising fat, oil and/or grease, said process comprising the steps of:
   (i) initial heating of the mixture so that it is flowable;
   (ii) acidifying the mixture;
   (iii) homogenising the mixture after acidification and prior to separation, wherein homogenisation comprises injecting steam into the mixture at a pressure of between 5 bar(g) (600 kPa) and 7 bar(g) (800 kPa) and agitation;
   (iv) separating the mixture into a solid fraction, an organic liquid fraction and an aqueous liquid fraction;
   (v) removing said solid and said aqueous liquid fractions from the mixture; and
   (vi) filtering the mixture using a rotary vacuum filter after removing said solid and said aqueous liquid fractions therefrom.

2. A process as claimed in claim 1, wherein initial heating of the mixture so that it is flowable comprises heating the mixture to between 55° C. and 65° C.

3. A process as claimed in claim 1, wherein the acidification comprises adjusting the pH to less than or equal to approximately pH 5.

4. A process as claimed in claim 1, wherein the acidification comprises adding acid to the mixture at a rate of between 1.5 kg per hour to 2.5 kg per hour.

5. A process as claimed in claim 4, wherein the acidification comprises adding water to the mixture at a rate of between 80 kg per hour to 100 kg per hour.

6. A process as claimed in claim 1, said process comprising the further step of pasteurising the mixture, optionally before the mixture is acidified.

7. A process as claimed in claim 6, wherein pasteurisation comprises heating the mixture to between 90° C. and 100° C.

8. A process as claimed in claim 6, wherein pasteurisation comprises heating the mixture for between 4 hours and 6 hours.

9. A process as claimed in claim 1, said process comprising the further step of removing debris from the mixture after initial heating and before acidification.

10. A process as claimed in claim 1, wherein separation comprises the simultaneous separation and discharge of said solid fraction, organic liquid fraction and aqueous liquid fraction.

11. A process as claimed in claim 1, wherein the separation is carried out using a three phase separation unit.

12. A process as claimed in claim 11, wherein the three phase separation unit is a horizontal decanter centrifuge.

13. A process as claimed in claim 11, wherein the three phase separation unit is a counter current decanter centrifuge.

14. A process as claimed in claim 11, wherein the three phase separation unit is operated at a bowl speed of from 3,000 to 4,000 RPM.

15. A process as claimed in claim 11, wherein the three phase separation unit is operated at a scroll speed of from 10 to 20 RPM.

16. A process as claimed in claim 1, wherein homogenisation comprises heating the mixture to between 85° C. and 95° C.

17. A process as claimed in claim 1, wherein the rotary vacuum filter comprises a layer of wood flour around the circumference thereof, and through which the mixture is filtered.

18. A process as claimed in claim 17, wherein the wood flour is cellulose fibre.

19. A process as claimed in claim 1, wherein the mixture is heated to between 65° C. and 85° C.

20. A process as claimed in claim 1, wherein the rotary vacuum filter is operated at a cutting rate of from 100 to 200 micrometers per revolution.

21. A process as claimed in claim 1, wherein the rotary vacuum filter is operated at rotational speed of from 1 to 2.5 RPM.

22. A process as claimed in claim 1, said process comprising the further step of recovery of organic liquids from aqueous liquids.

23. A process as claimed in claim 22, wherein the recovery comprises a dissolved air flotation process.

24. A process as claimed in claim 22, wherein the mixture is retained at a temperature of approximately 45° C. or less.

25. A process as claimed in claim 1, wherein the separating of the mixture into a solid fraction, an organic liquid fraction and an aqueous liquid fraction is subsequent to the acidification step.

26. A process as claimed in claim 1, wherein the removal of the solid and aqueous liquid fractions from the mixture is subsequent to the acidification step.

27. A process as claimed in claim 1, wherein the process comprises the additional step of initial separation of the mixture into an initial solid fraction, an initial organic liquid fraction and/or an initial aqueous liquid fraction, before the acidification step.

28. The process as claimed in claim 1, wherein the process comprises the additional step of initial removal of the initial solid and/or initial aqueous liquid fractions from the mixture, before the acidification step.

* * * * *